(12) United States Patent
Rommens et al.

(10) Patent No.: US 11,510,907 B2
(45) Date of Patent: Nov. 29, 2022

(54) MODIFIERS OF CFTR-DIRECTED THERAPY

(71) Applicants: THE HOSPITAL FOR SICK CHILDREN, Toronto (CA); THE GOVERNING COUNCIL OF THE UNIVERSITY OF TORONTO, Toronto (CA)

(72) Inventors: Johanna M. Rommens, Toronto (CA); Lisa Strug, Toronto (CA); Lei Sun, Toronto (CA)

(73) Assignees: The Hospital for Sick Children, Toronto (CA); The Governing Council of the University of Toronto, Toronto (CA)

( * ) Notice: Subject to any disclaimer, the term of this patent is extended or adjusted under 35 U.S.C. 154(b) by 102 days.

(21) Appl. No.: 17/006,474

(22) Filed: Aug. 28, 2020

(65) Prior Publication Data

US 2020/0390750 A1 Dec. 17, 2020

Related U.S. Application Data

(63) Continuation of application No. 15/756,791, filed as application No. PCT/CA2016/051044 on Sep. 2, 2016, now abandoned.

(60) Provisional application No. 62/213,399, filed on Sep. 2, 2015.

(51) Int. Cl.

| | |
|---|---|
| *C12Q 1/6883* | (2018.01) |
| *C12Q 1/68* | (2018.01) |
| *A61K 31/4245* | (2006.01) |
| *A61K 31/47* | (2006.01) |
| *G01N 33/48* | (2006.01) |
| *C07K 14/705* | (2006.01) |
| *C07D 271/06* | (2006.01) |
| *C07D 405/12* | (2006.01) |
| *C07D 215/233* | (2006.01) |
| *A61P 11/00* | (2006.01) |
| *A61K 31/443* | (2006.01) |
| *G01N 33/68* | (2006.01) |

(52) U.S. Cl.
CPC ........ *A61K 31/4245* (2013.01); *A61K 31/443* (2013.01); *A61K 31/47* (2013.01); *A61P 11/00* (2018.01); *C07D 215/233* (2013.01); *C07D 271/06* (2013.01); *C07D 405/12* (2013.01); *C07K 14/705* (2013.01); *C12Q 1/68* (2013.01); *C12Q 1/6883* (2013.01); *G01N 33/48* (2013.01); *G01N 33/6872* (2013.01); *G01N 33/6893* (2013.01); *C12Q 2600/106* (2013.01); *C12Q 2600/156* (2013.01); *C12Q 2600/158* (2013.01); *G01N 2800/12* (2013.01)

(58) Field of Classification Search
None
See application file for complete search history.

(56) References Cited

U.S. PATENT DOCUMENTS

2013/0274132 A1 10/2013 Strug et al.

FOREIGN PATENT DOCUMENTS

| CN | 105463094 B | 9/2018 |
|---|---|---|
| WO | 03074664 A2 | 9/2003 |

OTHER PUBLICATIONS

Mall (Journal of Cystic Fibrosis 14 (2015) pp. 561-570).*
Alton et al., "Repeated Nebulisation of Non-Viral CFTR Gene Therapy in Patients With Cystic Fibrosis: A Randomised, Double-Blind, Placebo-controlled, Phase 2b Trial," The Lancet Respiratory Medicine, Jul. 2015, vol. 3 (9), pp. 684-691.
Anagnostopoulou et al., "SLC26A9-Mediated Chloride Secretion Prevents Mucus Obstruction in Airway Inflammation," The Journal of Clinical Investigation, Oct. 2012, vol. 122 (10), pp. 3629-3634.
Avella et al., "SLC26A9 Stimulates CFTR Expression and Function in Human Bronchial Cell Lines," Journal of Cellular Physiology, Jan. 2011, vol. 226 (1), pp. 212-223.
Bertrand et al., "SLC26A9 is a Constitutively Active, CFTR-Regulated Anion Conductance in Human Bronchial Epithelia," The Journal of General Physiology, May 2009, vol. 133 (4), pp. 421-438.
Blackman et al., "Genetic Modifiers of Cystic Fibrosis-related Diabetes," Diabetes, Oct. 2013, vol. 62 (10), pp. 3627-3635.
Bobadilla et al., "Cystic Fibrosis: A Worldwide Analysis of CFTR Mutations—Correlation With Incidence Data and Application to Screening," Human Mutations, Jun. 2002, vol. 19 (6), pp. 575-606.
Bompadre et al., "G551D and G1349D, Two CF-associated Mutations in the Signature Sequences of CFTR, Exhibit Distinct Gating Defects," The Journal of General Physiology, Apr. 2007, vol. 129 (4), pp. 285-298.
Chang et al., "Slc26a9 is Inhibited by the R-region of the Cystic Fibrosis Transmembrane Conductance Regulator via the STAS Domain," Journal of Biological Chemistry, Oct. 2009, vol. 284 (41), pp. 28306-28318.
Corvol et al., "Genome-Wide Association Meta-analysis Identifies Five Modifier Loci of Lung Disease Severity in Cystic Fibrosis," Nature Communications, Sep. 2015, vol. 6, 8 pages.
Dorfman et al., "Modulatory Effect of the SLC9A3 Gene on Susceptibility to Infections and Pulmonary Function in Children With Cystic Fibrosis," Pediatric Pulmonology, Apr. 2011, vol. 46 (4), pp. 385-392.

(Continued)

*Primary Examiner* — Amanda Haney
(74) *Attorney, Agent, or Firm* — Borden Ladner Gervais LLP; Graeme R. B. Boocock

(57) ABSTRACT

Described herein is a genetic modifier of cystic fibrosis (CF), which may serve as a predictor of the efficacy of a CFTR-directed therapy. SNPs rs7512462 or rs2869027 in non-coding regions of SLC26A9 are shown to correlate with CF lung disease severity in patients having CFTR mutations that leave protein at the cell surface, e.g. gating mutations such as G551D. It is also shown that patient response to Ivacaftor correlates with SLC26A9 genotype. Given the biology of SLC26A9, risk alleles of SLC26A9 should correlate with reduced SLC26A9. SLC26A9 activity (marked by e.g. genotype or expression level) is therefore a predictor of treatment efficacy for any CFTR-directed therapeutic, such as Ivacaftor or Lumacaftor. Associated methods of selecting and treating patients are described, along with related kits, uses, and drug discovery platforms.

10 Claims, 5 Drawing Sheets

(56) References Cited

OTHER PUBLICATIONS

European Application No. 16840481.2, Communication pursuant to Article 94(3), dated Nov. 4, 2020.
European Patent Application No. 16840481.2, Extended European Search Report dated Feb. 5, 2019.
International Patent Application No. PCT/CA2016/051044, International Preliminary Reporton Patentability dated Mar. 15, 2018.
International Patent Application No. PCT/CA2016/051044, International Search Report and Written Opinion dated Dec. 12, 2016.
Kulich et al., "Disease-Specific Reference Equations for Lung Function in Patients with Cystic Fibrosis," American Journal of Respiratory and Critical Care, Oct. 2005, vol. 172 (7), pp. 885-891.
Li et al., "Unraveling the Complex Genetic Model for Cystic Fibrosis: Pleiotropic Effects of Modifier Genes on Early Cystic Fibrosis-related Morbidities," Human Genetics, Feb. 2014, vol. 133 (2), pp. 151-161.
Liu et al., "Loss of Slc26a9 Anion Transporter Alters Intestinal Electrolyte and HCO3(−) Transport and Reduces Survival in CFTR-Deficient Mice," Pflügers Archiv : European Journal of Physiology, Jun. 2015, vol. 467 (6), pp. 1261-1275.
Mall et al., "Targeting Ion Channels in Cystic Fibrosis", Journal of Cystic Fibrosis, Jun. 23, 2015, vol. 14 (5), pp. 561-570.
Miller et al., "Variants in Solute Carrier SLC26A9 Modify Prenatal Exocrine Pancreatic Damage in Cystic Fibrosis," The Journal of Pediatrics, May 2015, vol. 166 (5), pp. 1152-1157.
Ousingsawat et al., "Differential Contribution of SLC26A9 to Cl(−) Conductance in Polarized and Non-Polarized Epithelial Cells," Journal of Cellular Physiology, Jun. 2012, vol. 227 (6), pp. 2323-2329.
Ramsey et al., "A CFTR Potentiator in Patients with Cystic Fibrosis and the G551D Mutation," New England Journal of Medicine, Jan. 2011, vol. 365 (18), pp. 1663-1672.
Soave et al., "A Joint Location-Scale Test Improves Power to Detect Associated SNPs, Gene Sets, and Pathways," The American Journal of Human Genetics, Jul. 2015, vol. 97 (1), pp. 125-138.
Soave et al., "Evidence for a Causal Relationship Between Early Exocrine Pancreatic Disease and Cystic Fibrosis-Related Diabetes: A Mendelian Randomization Study," Diabetes, Jun. 2014, vol. 63 (6), pp. 2114-2119.
Sun et al., "Multiple Apical Plasma Membrane Constituents Are Associated With Susceptibility to Meconium Ileus in Individuals With Cystic Fibrosis," Nature Genetics, May 2012, vol. 44 (5), pp. 562-569.
Taylor et al., "A Novel Lung Disease Phenotype Adjusted for Mortality Attrition for Cystic Fibrosis Genetic Modifier Studies," Pediatric Pulmonology, Sep. 2011, vol. 46 (9), pp. 857-869.
U.S. Appl. No. 15/756,791, Non-Final Office Action dated Oct. 2, 2019.
U.S. Appl. No. 15/756,791, Advisory Office Action dated Aug. 27, 2020.
U.S. Appl. No. 15/756,791, Final Office Action dated Apr. 28, 2020.
Wainwright et al., "Lumacaftor-Ivacaftor in Patients with Cystic Fibrosis Homozygous for Phe508del CFTR," New England Journal of Medicine, May 2015, vol. 373 (18), pp. 220-231.
Wright et al., "Genome-Wide Association and Linkage Identify Modifier Loci of Lung Disease Severity in Cystic Fibrosis at 11p13 and 20q13.2," Nature Genetics, Jun. 2011, vol. 43 (6), pp. 539-546.

\* cited by examiner

MODIFIERS OF CFTR-DIRECTED THERAPY

CROSS-REFERENCE TO RELATED APPLICATION

This is a continuing application of U.S. patent application Ser. No. 15/756,791 filed on Mar. 1, 2018, which was a national phase entry of PCT Application No. CA2016/051044, which was filed on Sep. 2, 2016, and which claimed priority from U.S. Provisional Application No. 62/213,399 filed on Sep. 2, 2015, the contents of all of which are hereby incorporated by reference.

FIELD

The present disclosure relates generally to modifiers of cystic fibrosis. More particularly, the present disclosure relates to modifiers of CFTR-directed therapy.

BACKGROUND

Cystic Fibrosis (CF [MIM:219700]) is a common life-limiting genetic disease that is caused by mutations in the cystic fibrosis transmembrane conductance regulator (CFTR [MIM:602421]) gene. CF affects multiple organs including the pancreas, the intestine, and the lungs. Meconium ileus (intestinal obstruction at birth) and severe pancreatic disease leading to pancreatic insufficiency occur early in life, while the majority of CF-associated mortality is due to respiratory failure as a result of chronic airway infections leading to reduced lung function and repeated pulmonary exacerbations later in the course of disease. Individuals with the same CFTR mutations have variable disease across the CF-affected organs, suggesting that environmental factors along with other genes beyond the causal CFTR, referred to as modifier genes, can contribute to CF disease severity.

CFTR is an anion channel present in the epithelial membrane. There have been more than 1900 mutations reported in the CFTR gene, however fewer than 200 of these variants account for 96% of CF-causing alleles. CF-causing alleles affect the amount of protein and/or the function of the channel at the cell surface. For example, the most common CF-causing allele is a three base pair deletion resulting in the loss of a phenylalanine residue at position 508 in the CFTR protein, termed Phe508del. Phe508del represents about 70% of all CF-causing alleles with 45% of CF patients being homozygous for Phe508del. The Phe508del mutation disrupts CFTR chloride transport activity by reducing protein levels at the epithelial membrane due to a processing defect, and for the protein that does reach the cell surface the channel-open probability of the protein is reduced. In contrast, the missense mutation G551D, present on at least one allele in about 4-5% of individuals with CF (with varying geographical frequency), eliminates the ability of ATP to increase the channel activity, and the observed activity is ~100-fold smaller than wild-type CFTR. Consequently, G551D is termed a "gating mutation".

Modifier genes that contribute to CF-disease in the intestine, the lungs, the exocrine pancreas, the endocrine pancreas and others have been reported in individuals with severe CFTR mutations. These studies mostly include individuals with any two severe loss-of-function CFTR mutations, such as Phe508del, the majority of which result in little or no CFTR protein at the cell surface. Pleiotropy across multiple CF-affected organs is evident; for example, SLC9A3 and SLC6A14 contribute to CF lung and intestinal disease, while SLC26A9 appears to contribute to early-onset CF phenotypes in the gastrointestinal tract, but not the lungs (Li et al 2013; Sun et al 2012; Miller et al 2015; Soave et al 2014; Corvol et al 2015; Blackman et al 2013).

Treatment of CF has traditionally focused on lessening the manifestations of CF disease in the affected organs, rather than addressing the underlying cause of disease by targeting the dysfunctional CFTR protein itself. Recently, CFTR-directed therapies have become available.

Ivacaftor was the first drug to successfully target the CFTR protein itself, and to increase the amount of time that activated CFTR channels at the cell surface remain open to aid transport of anions (e.g. Cl– and HCO3–) across the apical membrane. Ivacaftor was shown to significantly improve lung function, on average, as measured by percent-predicted forced expiratory volume in 1s (FEV1pp) in individuals with a G551D-CFTR protein. An improvement of greater than 10 percentage points in FEV1pp from baseline to measurement at 24 weeks was observed, on average, between the Ivacaftor and placebo groups, and Ivacaftor is now approved for use by multiple international regulatory agencies in CF individuals with G551D or other gating mutations. However, drug response is highly variable.

More recently, Ivacaftor in combination with Lumacaftor—the latter being a CFTR corrector that improves the Phe508del CFTR misprocessing and increases the amount of cell surface-localized protein—has resulted in improved clinical outcomes in clinical trial. Although important, these improvements are much more modest than those observed in Ivacaftor treated individuals with the G551D-CFTR protein. Patient response was again variable.

In individuals with a G551D allele treated with Ivacaftor, or for those homozygous for Phe508del on Lumacaftor-Ivacaftor combination therapy, average improvements in outcomes are statistically significant. However, not all individuals respond to their respective treatments equally, with widespread variability in response observed in both CFTR mutation groups. The factors that explain this variability remain unknown, although there are many explanations hypothesized including drug metabolism, compliance, and modifier genes. These CFTR-directed treatments are, in turn, extremely costly.

There remains a need for predictors of treatment efficacy in CF.

SUMMARY

It is an object of the present disclosure to obviate or mitigate at least one disadvantage of previous approaches.

In one aspect, there is provided a method of selecting a cystic fibrosis patient for treatment with a CFTR-directed therapy, the method comprising steps of determining an activity level of SLC26A9 in a sample obtained from said patient; and selecting said patient for treatment with said CFTR-directed therapy based on the activity level.

In another aspect, there is provided a method of predicting treatment response of a cystic fibrosis patient to a CFTR-directed therapy, the method comprising steps of determining an activity level of SLC26A9 in a sample obtained from said patient; and predicting the treatment response based on the activity level.

In another aspect, there is provided a method of treating a cystic fibrosis patient with a CFTR-directed therapy, the method comprising steps of determining an activity level of SLC26A9 in a sample obtained from said patient; selecting said patient for treatment with said CFTR-directed therapy based on the activity level; and treating said selected patient with said CFTR-directed therapy.

In another aspect, there is provided a kit for use in selecting a cystic fibrosis patient for treatment with a CFTR-directed therapy, the kit comprising reagents for determining an activity level of SLC26A9 in a sample obtained from said patient; and instructions for selecting said patient for treatment with the CFTR-directed therapy based on the activity.

In another aspect, there is provided a kit for use in predicting treatment response of a cystic fibrosis patient to a CFTR-directed therapy, the kit comprising reagents for determining an activity level of SLC26A9 in a sample obtained from said patient; and instructions for predicting the treatment response based on the activity.

In another aspect, there is provided a kit for use in treating a cystic fibrosis patient for with a CFTR-directed therapy, the kit comprising reagents for determining an activity level of SLC26A9 in a sample obtained from said patient; and instructions for selecting said patient for treatment with said CFTR-directed therapy based on the activity, and treating said selected patient with said CFTR-directed therapeutic agent.

In another aspect, there is provided a use of a CFTR-directed therapy for treatment of a cystic fibrosis patient having an SLC26A9 activity that exceeds a threshold.

In another aspect, there is provided a use of a CFTR-directed therapy for preparation of a medicament for treatment of a cystic fibrosis patient having an SLC26A9 activity that exceeds a threshold.

In another aspect, there is provided a CFTR-directed therapy for use in treatment of a cystic fibrosis patient having an SLC26A9 activity that exceeds a threshold.

In another aspect, there is provided a method of identifying a candidate compound for treating cystic fibrosis (CF) comprising measuring a first level CFTR activity in a cell, contacting the cell with a test compound, measuring a second level of CFTR activity in the cell, and identifying said compound as a candidate compound for treating CF if the second level of CFTR activity exceeds the first level, wherein the cell exhibits increased SLC26A9 activity relative to a control.

In another aspect, there is provided a method of treating a cystic fibrosis (CF) patient comprising administering to the patient an SLC26A9-directed therapy.

In another aspect, there is provided a use of an SLC26A6-directed therapy for treatment of cystic fibrosis (CF) in a patient.

In another aspect, there is provided a use of an SLC26A6-directed therapy for preparation of a medicament for treatment of cystic fibrosis (CF) in a patient.

In another aspect, there is provided an SLC26A6-directed therapy for use in treatment of cystic fibrosis (CF) in a patient.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
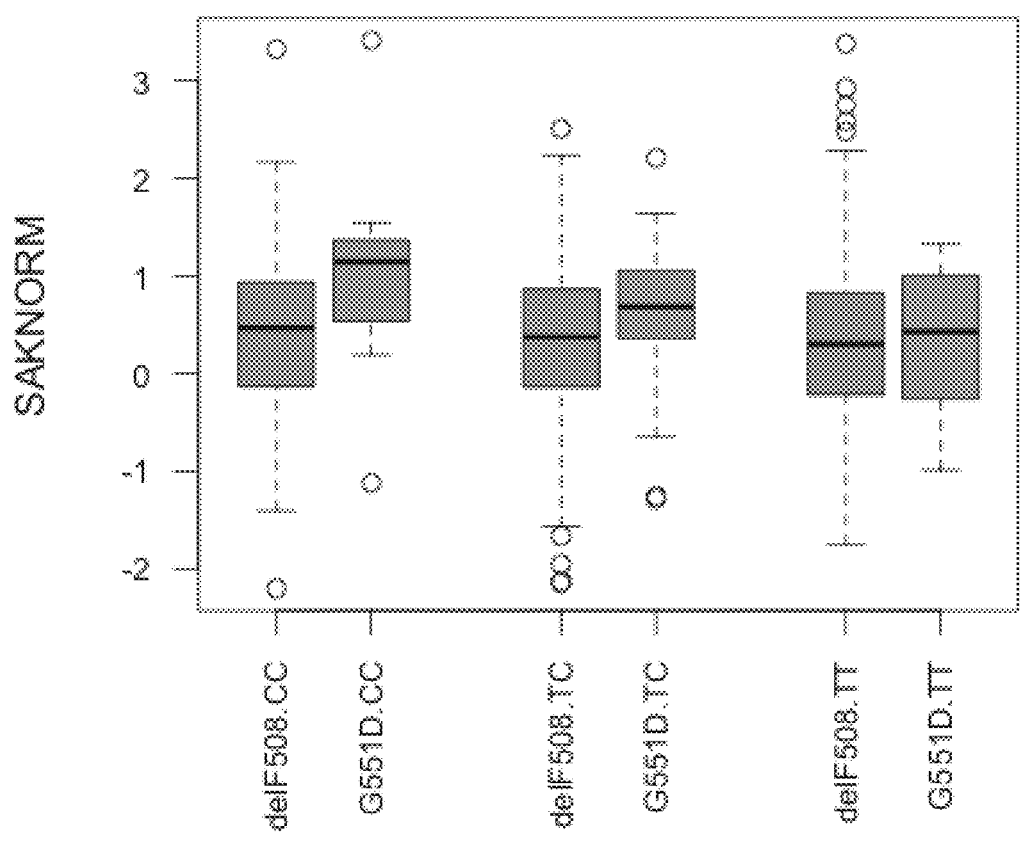
FIG. 1 depicts a boxplot of Saknorm grouped by rs7512462.

Described herein is a genetic modifier of cystic fibrosis (CF), which may serve as a predictor of the efficacy of a CFTR-directed therapy. Example SNPs rs7512462 or rs2869027 in non-coding regions of SLC26A9 are shown to correlate with CF lung disease severity in patients having CFTR mutations that leave protein at the cell surface. It is also shown that patient response to Ivacaftor correlates with SLC26A9 genotype. Given the biology of SLC26A9, risk alleles of SLC26A9 should correlate with reduced SLC26A9 activity. SLC26A9 activity (marked by e.g. genotype or expression level) is therefore expected to be a predictor of treatment efficacy for any CFTR-directed therapeutic, such as Ivacaftor, Lumacaftor, and combinations thereof.

Methods

In a first aspect, there is provided a method of selecting a cystic fibrosis patient for treatment with a CFTR-directed therapy, the method comprising steps of determining an activity level of SLC26A9 in a sample obtained from said patient; and selecting said patient for treatment with said therapy based on the activity level.

In a second aspect, there is provided a method of predicting treatment response of a cystic fibrosis patient to a CFTR-directed therapy, the method comprising steps of determining an activity level of SLC26A9 in a sample obtained from said patient; and predicting the treatment response based on the activity level.

In a third aspect, there is provided a method of treating a cystic fibrosis patient with a CFTR-directed therapy, the method comprising steps of determining an activity level of SLC26A9 in a sample obtained from said patient; selecting said patient for treatment with said therapy based on the activity level; and treating said selected patient with said therapy.

Ensuing embodiments are to be understood as being relevant to the above aspects, as well as ensuing aspects and embodiments.

By the term "CFTR-directed therapy" as used herein is meant any therapy or therapeutic agent that increases the amount or activity of CFTR protein at a cell surface. The aim of such therapies is to improve CF clinical manifestations, such as lung disease. Therapeutic agents encompass any molecule or composition that, for example, improves or corrects the expression, processing, folding, stability, or activity of the CFTR protein; that delivers the CFTR protein; or that decreases or inhibits the turnover of the CFTR protein. Likewise, such agents are understood to encompass any agent that increases or corrects the transcription, processing, stability, or translation of the CFTR mRNA; or that decreases or inhibits the turnover of CFTR mRNA such that more protein is produced. Such agents may act directly on CFTR, or may act indirectly through, e.g. associated or interacting proteins. Suitable therapeutic agents may be, for example, small molecule drugs or biologics.

Intended therapeutic agents should be understood to encompass CFTR modulators, including activators, potentiators, and correctors. Activators are agents that can stimulate CFTR channel function by means of increasing intracellular cAMP/cGMP levels. Potentiators are agents that can increase the channel gating activity of cell-surface localized CFTR, thereby enhancing its ion transport capability. Correctors act by increasing the amount of functional CFTR at the cell surface, enables enhanced ion transport. CFTR modulators include, for example, Ataluren (a CFTR corrector), Ivacaftor (a CFTR potentiator), and Lumacaftor (a CFTR corrector).

Intended therapies and therapeutic agents are also understood to encompass gene therapy and agents used for gene therapy, such as, e.g., retroviral vectors or genome editing reagents. One gene therapy protocol is described by Alton et al (2015).

Intended therapeutic agents also encompass agents and treatments that increase the effective amount of CFTR at the cell surface, e.g. by restoring epithelial integrity or function. Such agents may include those administered to improve CF lung function, e.g. by clearing mucus or increasing the air-surface liquid interface (e.g. DNAse, hypotonic saline, etc.).

By the term "activity level" of SLC26A9 used herein is meant the normal activity or activities of SLC26A9 that enhance(s) or improve(s) CFTR activity, or that compensate(s) or complement(s) for CFTR deficiency. For example, SLC26A9 may increase CFTR activity, or its own function may partially compensate for CFTR deficiency. Such activities are to be understood to encompass the possibility of interaction with CFTR. They may also encompass function as an anion channel, a transporter (e.g. of sulphate), or an exchanger. Some SLC26A9 activities can be measured directly, e.g. in a targeted in vitro assay, though it is often more convenient or practical to assess activity indirectly, by measuring expression level or an indicator thereof.

By "SLC26A9", as used herein, is meant the human gene, mRNA, or protein having SLC26A9 (solute carrier family 26 (anion exchanger), member 9) as an accepted name, and generally corresponding to the transcript reference sequences deposited in GenBank under accessions NM_052934 (isoform A) and/or NM_134325 (isoform B). The term, as used herein, is intended to encompass all functional isoforms, sequence variants, fragments, and post-translational modifications, e.g., as seen in a relevant population, cell type, stage of development, or state of differentiation.

In one embodiment, the method further comprises clinically monitoring a patient predicted to have a poor treatment response.

The term "monitoring", used herein, encompasses clinical monitoring of e.g. disease severity or progression.

By "poor treatment response", as used herein, is meant a patient that is predicted to not respond to treatment, or that is predicted to respond poorer than average. The mode of prediction could be adjusted according to requirements. For example, one or more samples from patients having one or two of the protective alleles described herein (e.g., C in rs7512462 or G in rs2869027) could serve as a benchmark of a "good outcome", while patient with one or two of the risk alleles (e.g., T in rs7512462 or C in rs2869027) could serve as a benchmark for a "poor outcome".

In one embodiment, the method further comprises a step of treating a patient predicted to have a poor treatment response with another therapy. For example, a primary therapy may be combined with a complementary therapy. The term "another therapy" is intended to mean an alternative or different therapy from the one for which poor outcome is predicted, or a therapy that complements a primary therapy ("complementary therapy"). Such therapies may include other drugs, supportive therapies, gene therapy, or combinations thereof. Such therapies may include saline rinses, DNAse treatment, administration of antibiotics (such as prophylactic treatment), and/or physiotherapy.

In one embodiment, the treatment is a treatment of CF lung disease, lung disease being the major cause of morbidity and mortality in CF. The term "CF lung disease", as used herein, is intended to encompass developing lung disease, chronic lung disease, acute episodes, and progressive aspects of lung disease in CF.

In one embodiment, the method comprises measuring an expression level of SLC26A9 protein or mRNA, and selecting said patient for treatment or predicting a positive response to treatment if said expression level exceeds a threshold.

By the term "threshold" used herein is meant a value that is selected to discriminate between those patients who would likely benefit by receiving treatment with the CFTR-directed therapeutic, and those patients who would likely not. A threshold may be set according to requirements, e.g. to achieve a particular sensitivity or specificity. A threshold may be set according to the details of a particular assay. A threshold may also be set according to, e.g., the nature of a sample or the population from which a sample is drawn (e.g. age, ethnicity, etc.). As described below, those having genotype TT at single nucleotide polymorphism (SNP) rs7512462, or genotype CC at SNP rs2869027 tend to have worse treatment outcome. Accordingly, in some instances, a threshold may be established using data from individuals having one or both of these SNP genotypes indicative of worse treatment outcome. A threshold may, however, be set according to the SNP(s) that is/are selected for the method. As an example, an average level of activity of such individuals may serve as a suitable threshold (subject to statistical, sensitivity, and specificity requirements) beyond which a patient is selected.

Any of a number of extant methods may be employed for measuring protein expression, such as immunoassays and mass spectrometry-based methods. In one embodiment, the expression level of the SLC26A9 protein is measured by an immunoassay.

Likewise, any of a number of known methods may be employed for measuring mRNA expression. Assays for measuring RNA expression may measure the RNA itself, or may measure cDNA derived therefrom. In one embodiment, the SLC26A9 RNA is measured by an assay comprising primer extension or nucleic acid hybridization. Suitable assays may include, for example, RNASeq, Northern analysis, quantitative or semi-quantitative RT-PCR, array-based hybridization, or mRNA counting. Suitable samples could include e.g. bronchiole scrapings, lung scrapings, or nasal scrapings.

In some embodiments, the method comprises determining SLC26A9 activity using a genetic marker indicative of activity. By "genetic marker indicative of activity", as used herein is meant any genetic variant that correlates with or causes altered SLC26A9 activity. Such variants could be in the SLC26A9 gene itself, including coding and non-coding regions. Variants in coding regions could include both silent nucleotide substitutions and/or those leading to alterations of the amino acid sequence. Such variants may encompass "regulatory" variants that affect mRNA levels. Variants can also be outside the SLC26A9 gene, and may be located in regulatory elements or microRNAs. Variants may also be in or around other genes that impact SLC26A9 activity. Variants can increase or decrease SLC26A9 activity, directly or indirectly.

For example, the activity level of SLC26A9 may be determined by determining a genotype of a single nucleotide polymorphism (SNP) indicative of SLC26A9 activity. In one embodiment, the SNP is rs7512462, and said patient is selected for treatment if the rs7512462 genotype is determined to be CC or TC. For rs7512462, T is considered to be the "risk allele" associated with worse lung disease and/or treatment efficacy, and predicted to be associated with lower SLC26A9 expression. C is considered to be a "protective allele". In one embodiment, the patient may be selected for treatment if the rs7512462 genotype is determined to be CC. In another example, the SNP is rs2869027, and said patient is selected for treatment if the rs2869027 genotype is determined to be GG or GC. For rs2869027, C is considered to be the "risk allele" associated with worse lung disease and/or treatment efficacy, and predicted to be associated with lower SLC26A9 expression. G is considered to be the "protective allele". In one embodiment, the patient is selected for treatment if the rs2869027 genotype is determined to be GG.

The term "efficacy" as used herein is intended to mean improvement in at least one clinical symptom of CF. Efficacy is also intended to encompass a self-reported improvement. Improved efficacy may lead to reduced morbidity or mortality for a group of patients receiving a particular therapy or therapeutic.

In one embodiment, the genotype of the above SNP is directly determined. It will be appreciated that the genotype of the two example SNPs may also be indirectly determined by genotyping a nearby SNP that may serve as a proxy (herein termed a "proxy SNP") for the above-defined SNP (herein termed a "primary SNP"). This is due to the propensity of nearby SNPs to be co-inherited, and due to blocks of linkage disequilibrium in the genome. Accordingly, rs7512462 and rs2869027 are merely exemplary of useful genetic variants. Suitable proxy SNPs may be selected using extant physical maps, genetic maps, SNP database, etc. Suitable proxy SNPs may be those nearby in physical distance, for example those up to 100 bp, 200 bp, 500 bp, 1 kb, 2 kb, 3 kb, 4 kb, 5 kb, 6 kb, 7 kb, 8 kb, 9 kb, 10 kb, 50 kb, or farther away from the primary SNP. A suitable proxy SNP may also be up to 1 kb, 2 kb, 3 kb, 4 kb, 5 kb, 6 kb, 7 kb, 8 kb, 9 kb, 10 kb, 50 kb, or farther away from the 5' or 3' end of the SLC26A9 gene. Another way to identify proxy SNPs is through linkage disequilibrium. In another embodiment, the genotype of one of the above SNPs may be indirectly determined by directly determining the genotype of a proxy SNP in linkage disequilibrium (LD) with said SNP. Suitable proxy SNPs may be those having a D' value of 0.85, 0.9, 0.91, 0.92, 0.93, 0.94, 0.95, 0.96, 0.97, 0.98, or 0.99. For example, a 0.85 D' value may serve as a useful threshold for selecting proxy SNPs in LD with the primary SNP. Alternatively, a D' of 0.9 may be used. LD can be assessed according to the relevant population. Risk alleles for a proxy SNP can be determined by examining genotype association with the primary SNP. One could readily determine the risk allele and protective allele for a given SNP based, for example, on its D' in respect of a primary SNP, and genotype information thereof. It is to be understood that a "proxy SNP" is simply one that is initially selected, e.g. based on distance from a primary SNP (or SLC26A9), using genetic or risk information derived the primary SNP, and/or based on how informative it is. Once selected, a proxy SNP could serve as a primary SNP, for example, if it is deemed to provide useful information itself (e.g. if it provides equal, additional, or different risk information compared to the primary SNP).

Merely as examples, proxy SNPs for rs7512462 may include rs7419153, rs1891309, rs1891310, rs1473537, rs34190121, rs72752927, rs72752928, rs66593238, rs9438407, rs12741299, rs34265780, rs66593238, rs1342063, rs1342064, rs4951271, rs4077468, rs4077469, rs2036100, or rs61814953.

Merely as examples, proxy SNPs for rs2869027 may include rs2903990, rs12031234, rs2282429, or rs2282430.

Any SNP genotyping method may be used to determine genotype at the relevant SNP. In one embodiment, SNP genotyping is accomplished using a method comprising hybridization of a probe or primer extension. Suitable hybridization probes or primers could be readily made based on the target sequences. Such methods may include, for example, those based on allele-specific hybridization, molecular beacons, microarrays, restriction fragment length polymorphisms (RFLPs), polymerase chain reaction (PCR), Flap endonuclease, primer extension, 5'-nuclease, oligonucleotide ligation, single strand conformation polymorphism (SSCP), temperature gradient electrophoresis, high performance liquid chromatography (HPLC), high-resolution melting, use of DNA mismatch-binding protein, SNPlex, or sequencing.

The term "mutation" as used herein with respect to CFTR is intended to encompass any genetic variant or sequence change (e.g. with respect to a prevailing or "wild type" allele) in or around the CFTR gene or its associated regulatory elements that, in trans with another established CF mutation, is associated with one or more clinical symptom of cystic fibrosis. For example, a mutation may be defined as one that causes an accepted clinical hallmark of the CF phenotype, such as a sweat chloride level of greater than or equal to 60 mmol/L.

In one embodiment, the method may be applied to a CF patient having at least one mutation resulting in residual CFTR protein at the cell surface.

By "residual protein at the cell surface" is meant protein that is detectable at the cell surface, e.g. in a suitable assay.

In one embodiment, the at least one mutation comprises a gating mutation in CFTR. Gating mutations include, for example, G178R, S549N, S549R, G551S, G1244E, S1251N, S1255P and G1349D. In one particular embodiment, the gating mutation is a G551D mutation in CFTR.

In one embodiment, the patient comprises a Phe508del mutation in CFTR.

In one embodiment, the CFTR-directed therapeutic comprises a small molecule drug. The drug may be a CFTR activator, potentiator, corrector, or a combination thereof. In one embodiment, the therapy comprises Ivacaftor (systematic name N-(2,4-Di-tert-butyl-5-hydroxyphenyl)-4-oxo-1,4-dihydroquinoline-3-carboxamide). Ivacaftor is also named Kalydeco™ or VX-770. In one embodiment, the therapy comprises Lumacaftor (systematic name 3-{6-{[1-(2,2-Difluoro-1,3-benzodioxol-5-yl)cyclopropanecarbonyl]amino}-3-methylpyridin-2-yl}benzoic acid). Lumacaftor is also named VX-809. In one embodiment, the therapy comprises Lumacaftor and Ivacaftor. A combination of these two drugs is marketed under the named Orkambi™. However, the combinations referred to herein are limited to any specific formulation marketed under this trade name name; the therapy may comprise other combinations of Ivacaftor and Lumacaftor. The therapy may comprise Ivacaftor in combination with another drug, such as a corrector that is not Lumacaftor. Likewise, the therapy may comprise Lumacaftor in combination with another drug, such as a potentiator that is not Ivacaftor. In one embodiment, the therapy comprises Ataluren. Ataluren is used to treat patients bearing nonsense mutations, and is also known as PTC124 (systematic name 3-[5-(2-Fluorophenyl)-1,2,4-oxadiazol-3-yl]benzoic acid). Ataluren is marketed under the trade name Translarna™.

Kits

There are also provided kits relating to the above methods.

In one aspect, there is provided a kit for use in selecting a cystic fibrosis patient for treatment with a CFTR-directed therapy, the kit comprising reagents for determining an activity level of SLC26A9 in a sample obtained from said patient; and instructions for selecting said patient for treatment with the CFTR-directed therapy based on the activity.

In another aspect, there is provided a kit for use in predicting treatment response of a cystic fibrosis patient to a CFTR-directed therapy, the kit comprising reagents for determining an activity level of SLC26A9 in a sample obtained from said patient; and instructions for predicting the treatment response based on the activity.

In another aspect, there is provided a kit for use in treating a cystic fibrosis patient for with a CFTR-directed therapy, the kit comprising reagents for determining an activity level of SLC26A9 in a sample obtained from said patient; and instructions for selecting said patient for treatment with said CFTR-directed therapy based on the activity, and treating said selected patient with said CFTR-directed therapy.

Ensuing embodiments are to be understood as being relevant to the above aspects, as well as other aspects and embodiments described herein.

In one embodiment, the instructions indicate that a patient predicted to have a poor treatment response should be clinically monitored.

In one embodiment, the instructions indicate that a patient predicted to have a poor treatment response should be treated with another therapy. For example, a primary therapy may be combined with a complementary therapy.

In one embodiment, the treatment is a treatment of CF lung disease.

In one embodiment, reagents comprise reagents for measuring an expression level of SLC26A9 protein or mRNA, and said instruction indicate to select said patient for treatment or to predict a positive response to treatment if said expression level exceeds a threshold.

Reagents for any one of a number of extant methods may be included in the kit for measuring protein expression, such as immunoassays and mass spectrometry-based methods. In one embodiment, the reagents comprise an antibody specific to the SLC26A9 protein.

Likewise, reagents for any one of a number of extant methods may be included in the kit for measuring mRNA expression. Assays for RNA expression may employ RNA itself, or cDNA derived therefrom. In one embodiment, the reagents comprise a nucleic acid probe or primer for measuring SLC26A9 mRNA. Suitable assays may include, for example, RNASeq, Northern analysis, quantitative or semi-quantitative RT-PCR, array-based hybridization, or mRNA counting.

In some embodiments, the kit comprises reagents for determining SLC26A9 activity by genotyping a genetic marker indicative of activity. For example, the kit may comprise reagents for genotyping a single nucleotide polymorphism (SNP) indicative of SLC26A9 activity. In one embodiment, the reagents are reagents for genotyping rs7512462, and the instructions indicate that the patient is to be selected for treatment or to predict a positive response to treatment if the rs7512462 genotype is determined to be CC or TC. In one embodiment, the instructions indicate that the patient is to be treated or to predict a positive response to treatment if the rs7512462 genotype is determined to be CC. In one embodiment, the instructions indicate that the patient is to be selected for treatment or to predict a positive response to treatment if at least one C allele is detected at rs7512462. In another embodiment, the reagents are for genotyping rs2869027, and the instructions indicate that the patient is to be selected for treatment or to predict a positive response to treatment if the rs2869027 genotype is determined to be GG or GC. In one embodiment, the instructions indicate that the patient is to be selected for treatment or to predict a positive response to treatment if the rs2869027 genotype is determined to be GG. In one embodiment, the instructions indicate that the patient is to be selected for treatment or to predict a positive response to treatment if at least one G allele is detected at rs2869027.

In one embodiment, the reagents are for directly genotyping the above SNP. However, it will be appreciated that the genotype of these SNPs may also be indirectly determined by genotyping a nearby SNP that may serve as a proxy for one of the above SNPs. Suitable proxy SNPs may be selected from extant physical maps, genetic maps, SNP database, etc. Suitable proxy SNPs may be those nearby in physical distance, for example those up to 1 kb, 2 kb, 3 kb, 4 kb, 5 kb, 6 kb, 7 kb, 8 kb, 9 kb, 10 kb, 50 kb, or farther away from the primary SNP. A suitable proxy SNP may also be up to 1 kb, 2 kb, 3 kb, 4 kb, 5 kb, 6 kb, 7 kb, 8 kb, 9 kb, 10 kb, 50 kb, or farther away from the 5' or 3' end of the SLC26A9 gene. In another embodiment, the reagents are for directly genotyping a proxy SNP in linkage disequilibrium (LD) with one of the above SNPs. Suitable proxy SNPs may be those having a D' value of 0.85, 0.9, 0.91, 0.92, 0.93, 0.94, 0.95, 0.96, 0.97, 0.98, or 0.99. For example, a 0.85 D' value may be a useful threshold for selecting proxy SNPs in LD with the primary SNP. LD can be assessed according to the relevant population. Risk alleles for a proxy SNP can be readily determined by examining genotype associate with the primary SNP.

Merely as examples, proxy SNPs for rs7512462 may include rs7419153, rs1891309, rs1891310, rs1473537, rs34190121, rs72752927, rs72752928, rs66593238, rs9438407, rs12741299, rs34265780, rs66593238, rs1342063, rs1342064, rs4951271, rs4077468, rs4077469, rs2036100, or rs61814953.

Merely as examples, proxy SNPs for rs2869027 may include rs2903990, rs12031234, rs2282429, or rs2282430.

Any SNP genotyping method may be used to determine genotype at the relevant SNP. In one embodiment, the reagents comprise a nucleic acid probe or primer. Suitable hybridization probes or primers could be readily made based on the target sequences. Reagents may encompass reagents for methods such as, for example, those based on allele-specific hybridization, molecular beacons, microarrays, restriction fragment length polymorphisms (RFLPs), polymerase chain reaction (PCR), Flap endonuclease, primer extension, 5'-nuclease, oligonucleotide ligation, single strand conformation polymorphism (SSCP), temperature gradient electrophoresis, high performance liquid chromatography (HPLC), high-resolution melting, use of DNA mismatch-binding protein, SNPIex, or sequencing.

In one embodiment, the kit is for use with a CF patient having at least one mutation resulting in residual CFTR protein at the cell surface. In one embodiment, the at least one mutation comprises a gating mutation in CFTR. Gating mutations include, for example, G178R, S549N, S549R, G551S, G1244E, S1251N, S1255P and G1349D. In one particular embodiment, the gating mutation is a G551D mutation in CFTR.

In one embodiment, the patient comprises a Phe508del mutation in CFTR.

In one embodiment, the CFTR-directed therapy comprises gene therapy.

In one embodiment, the CFTR-directed therapeutic comprises a small molecule drug. The drug may be a CFTR activator, potentiator, or corrector. In one embodiment, the therapy comprises Ivacaftor. Ivacaftor is also named Kalydeco™ or VX-770. In one embodiment, the therapy comprises Lumacaftor. Lumacaftor is also named VX-809. In one embodiment, the therapy comprises Lumacaftor and Ivacaftor. A combination of these two drugs is marketed under the named Orkambi™. However, the combinations referred to herein are limited to any specific formulation marketed under this trade name; the therapy may comprise other combinations of Ivacaftor and Lumacaftor. The therapy may comprise Ivacaftor in combination with another drug, such as a corrector that is not Lumacaftor. Likewise, the therapy may comprise Lumacaftor in combination with another drug, such as a potentiator that is not Ivacaftor. In one embodiment, the therapy comprises Ataluren. Ataluren is used to treat patients bearing nonsense mutations, and is also known as PTC124.

CFTR-Directed Therapeutics

In one aspect, there is provided a use of a CFTR-directed therapeutic for treatment of a cystic fibrosis patient having an SLC26A9 activity that exceeds a threshold.

In another aspect, there is provided a use of a CFTR-directed therapeutic for preparation of a medicament for treatment of a cystic fibrosis patient having an SLC26A9 activity that exceeds a threshold.

In an additional aspect, there is provided a CFTR-directed therapeutic for use in treatment of a cystic fibrosis patient having an SLC26A9 activity that exceeds a threshold.

The ensuing embodiment as to be understood to be applicable to above aspects, and other aspects and embodiments described herein.

In one embodiment, the cystic fibrosis patient has a measured expression level of SLC26A9 that exceeds a threshold.

In one embodiment, the cystic fibrosis patient has a SNP genotype indicative of SLC26A6 activity that exceeds the threshold. For example, the patient may have a SNP genotype of CC or TC at rs7512462. The patient may have a SNP genotype of CC at rs7512462. As another example, the patient may have a SNP genotype of GG or GC at rs2869027. The patient may have a SNP genotype of GG at rs2869027.

In one embodiment, the patient has at least one gating mutation in CFTR. The at least one gating mutation may be G551D.

In one embodiment, the patient comprises a Phe508del mutation in CFTR.

In one embodiment, the CFTR-directed therapy comprises a reagent for gene therapy.

In one embodiment, the CFTR-directed therapy comprises Ivacaftor.

In one embodiment, the CFTR-directed therapy comprises Lumacaftor.

In one embodiment, the CFTR-directed therapy comprises Ivacaftor and Lumacaftor.

In one embodiment, the CFTR-directed therapy comprises Ataluren.

In one embodiment, the treatment is treatment of CF lung disease.

Drug Discovery Platform

In one aspect, there is provided a method of identifying a candidate compound for treating cystic fibrosis (CF) comprising measuring a first level CFTR activity in a cell, contacting the cell with a test compound, measuring a second level of CFTR activity in the cell, and identifying said test compound as a candidate compound for treating CF if the second level of CFTR activity exceeds the first level, wherein the cell exhibits increased SLC26A9 activity relative to a control.

In one embodiment, the cell exhibits increased SLC26A9 expression compared to the control.

In one embodiment, the cell has a genotype CC or CT at rs7512462. For instance, the cell may have the genotype CC at rs7512462.

In one embodiment, the cell has a genotype GG or GC at rs2869027. For instance, the cell may have the genotype GG at rs2869027.

In one embodiment, the control is a control cell having a genotype TT at rs7512462 and/or CC at rs2869027.

In one embodiment, the cell comprises mutations in both copies of the CFTR gene.

In one embodiment, the cell comprises at least one gating mutation. The at least one gating mutation may be G551D.

In one embodiment, the cell comprises a Phe508del mutation in CFTR.

In one embodiment, the method is for identifying a candidate compound for treating CF lung disease.

SLC26A9-Directed Therapies

In one aspect, there is provided a method of treating a cystic fibrosis (CF) patient comprising administering to the patient an SLC26A9-directed therapy.

The term "SLC26A9-directed therapy" is defined similarly to the CFTR-directed therapy, described above. It is intended to encompass any therapy or therapeutic agent that ultimately increases the amount or activity of SLC26A9 protein. Therapeutic agents encompass any molecule or composition that, for example, improves or corrects the expression, processing, folding, stability, or activity of the SLC26A9 protein; or that decreases or inhibits the turnover of the SLC26A9 protein. Likewise, such agents are understood to encompass any agent that increases or promotes the transcription, processing, stability, or translation of the SLC26A9 mRNA; or that decreases or inhibits the turnover of SLC26A9 mRNA such that more protein is produced. Such agents may act directly on SLC26A9, or may act indirectly through, e.g. associated or interacting proteins. Suitable therapeutic agents may be, for example, small molecule drugs or biologics.

In one embodiment, the SLC26A9-directed therapy increases the expression of SLC26A9.

Synergistic effects could ensue by using an SLC26A9-directed therapy and a CFTR-directed therapy. In one embodiment, the method further comprises administering to the patient a CFTR-directed therapy. The CFTR-directed therapy comprises Ivacaftor, Lumacaftor, Ataluren, or a combination thereof.

In one embodiment, the patient has at least one gating mutation in CFTR. The at least one gating mutation may be G551D.

In one embodiment, the patient has a Phe508del mutation in CFTR.

Synergistic effects could ensue by using the SLC26A9-directed therapy in a patient having increased SLC26A9 activity relative to a control. For example, the patient could have increased SLC26A9 expression relative to a control. A suitable control could be obtained, for example, from an individual having genotype TT at rs7512462 or CC at rs2869027.

In one embodiment, the patient has a genotype of CC or CT at rs7512462.

In one embodiment, the patient has a genotype GG or GC at rs2869027.

In one embodiment, the method is for treating CF lung disease.

In other embodiments, it may be beneficial to use an SLC26A9-directed therapy to treat a patient having one or two SLC26A9 risk allele(s). For example, the patient may have TT at rs7512462 and/or CC at rs2869027. In these instances, administering an SLC26A9-directed therapy may help to reduce or mitigate effects the risk allele. In some embodiments, the method may comprise co-administering a CFTR-directed therapy, as described above. In some embodiments, the SLC26A9-directed therapy may be administered to a patient who has received, is receiving, or will receive a CFTR-directed therapy, as described above.

In another aspect, there is provided a use of an SLC26A6-directed therapy for treatment of cystic fibrosis (CF) in a patient.

In another aspect, there is provided a use of an SLC26A6-directed therapy for preparation of a medicament for treatment of cystic fibrosis (CF) in a patient.

In another aspect, there is provided an SLC26A6-directed therapy for use in treatment of cystic fibrosis (CF) in a patient.

The ensuing embodiments are relevant to the forgoing three "use" and "therapy for use", as well as other embodiments described herein.

In one embodiment, the SLC26A6-directed therapy increases the expression of SLC26A9.

In one embodiment, the patient is receiving a CFTR-directed therapy. The CFTR-directed therapy may comprise Ivacaftor, Lumacaftor, Ataluren, or a combination thereof.

In one embodiment, the patient has at least one gating mutation in CFTR. The at least one gating mutation may be G551D.

In one embodiment, the patient has a Phe508del mutation in CFTR.

In one embodiment, the patient has a genotype of CC or CT at rs7512462.

In one embodiment, the patient has a genotype GG or GC at rs2869027.

In one embodiment, the treatment is treatment of CF lung disease.

In other embodiments, it may be beneficial to use an SLC26A9-directed therapy to treat a patient having one or two SLC26A9 risk allele(s). The risk allele can be determined based on the SNP or proxy SNP used. For example, the patient may have TT at rs7512462 and/or CC at rs2869027. In these instances, an SLC26A9-directed therapy may be used to reduce or mitigate effects the risk allele. In some embodiments, the use may comprise using the SLC26A9-directed therapy with a CFTR-directed therapy. In some embodiments, the patient may be one also receiving (or who has previously received or who will receive) a CFTR-directed therapy, as described above.

EXAMPLES

Example 1

Association of SLC26A9 and Lung Disease in CF Patients with G551D Mutation

Patients and Samples

Individuals studied with CF included fifty-six who had a G551D allele and 1,108 who were homozygous for the Phe508del mutation; and that were both enrolled in the Canadian Gene Modifier study and had undergone genome-wide genotyping as part of ongoing gene modifier studies of the Canadian cohort (Dorfman et al 2011; Taylor et al 2011 Sun et al 2012).

Methods

Genotyping was performed genome-wide as part of the Canadian gene modifier study on the Illumina 610 Quad Bead chip and by Taqman genotyping (Sun et al 2012). In a subset of individuals on whom rs7512462 information was not available (n=6), the services of the Centre for Applied Genomics at the Hospital for Sick Children were employed to genotype rs7512462 using Taqman SNP genotyping and whole genome microarrays (Illumina Omni 2.5). DNA was extracted from either whole blood or from lymphoblasts.

For gene modifier studies, the lung function phenotype that was used was a Survival-adjusted averaged CF-specific FEV1 percentiles (Kulich et al 2005) that is then normalized (Saknorm). Since the CF population analyzed in the gene modifier studies included individuals from all age groups, and since there is differential mortality due to CF across different age groups, cohort-specific survival estimates were used to adjust CF-specific percentiles to ensure individuals' lung function phenotypes are comparable across different ages (Taylor et al 2011). Linear regression analysis assessed the relationship between Saknorm and rs7512462 in G551D mutation carriers, where rs7512462 was coded additively with respect to the number of T risk alleles. The T allele is referred to as the "risk allele" of rs7512462 since it was previously shown to associate with worse pancreatic disease at birth (Miller et al 2015) in CF, greater risk of meconium ileus at birth (Sun et al; 2012), and greater risk of CF-related diabetes (Blackman et al 2013). To determine whether the relationship between Saknorm and rs7512462 differs significantly depending on whether an individual carries a G551D allele or is homozygous for Phe508del, linear regression was used on the full sample of 1,164 individuals and included a covariate for CFTR genotype and its interaction with rs7512462 number of T risk alleles.

Results

FIG. 1 shows that the distribution of lung function in individuals homozygous for Phe508del appear similar regardless of rs7512462 genotype, whereas for those with at least one G551D CFTR allele or other gating mutation, lung function appears to be worse depending on the number of T alleles at SLC26A9 rs7512462. FIG. 1 also suggests that across all rs7512462 genotypes, G551D appears to have slightly better lung function on average that those with Phe508del.

These observations suggest that CFTR genotype is associated with lung function and that the effect of rs7512462 is different on Phe508del versus G551D mutations.

The T allele frequency was 0.62 in those with a G551D allele, and 0.59 in those homozygous for Phe508del. For individuals with at least one G551D CFTR allele or other gating mutation (n=56), each additional T allele at rs7512462 is associated with a ~0.32 unit decrease in Saknorm (beta=−0.3206, two-sided p=0.06 for T risk allele, n=56), which corresponds to a decrease of 0.1410 in a CF-specific percentile for an individuals with CF who is 18 years of, age. In a model that includes both individuals homozygous for Phe508del (n=1052) and individuals with at least one G551D mutation (n=56), having a G551D CFTR allele is associated with better lung function as measured by Saknorm (p=0.0198, beta=0.55315) as compared to individuals homozygous for Phe508del. Each additional SLC26A9 rs7512462 T allele is associated with worse lung function in G551D or other gating mutation carriers but not in those homozygous for Phe508del (interaction one-sided p=0.056).

Example 2

Association of SLC26A9 and Reduced Improvement from Ivacaftor

Patients and Samples

Of the 56 CF individuals in Example 1 with a G551D allele or other gating mutation (e.g. 1 individual with mutation S549N) and genome-wide genotyping, 11 were enrolled in an open-label study of Ivacaftor at the CF clinics of the Hospital for Sick Children or St. Michael's Hospital, and consented to have their clinical data linked to their genetic data from the Canadian Gene Modifier study. In a replication stage, 11 additional individuals on Ivacaftor with a G551D or other gating mutation (e.g. G178R) with baseline and post-treatment clinical data who were enrolled in the Canadian Gene Modifier study but who did not have genotype information were genotyped at rs7512462 and analyzed separately.

Methods

Genotyping was carried out as in Example 1.

Baseline measures of FEV1 percent predicted (FEV1pp) prior to treatment with Ivacaftor were obtained in addition to multiple other clinical measures. For inclusion in either the discovery or replication phases of the study, at least one FEV1 measurement post-treatment was required. The number of follow-up measurements ranged from 1-6, with 50% having 3 post-treatment measurements. Post treatment measurements were averaged, and the treatment response was defined as the difference between the average FEV1pp post treatment and the individuals' baseline FEV1pp prior to treatment, as in the Lumacaftor-Ivacaftor clinical trial.

Given the sample sizes and the presence of outliers in the data, robust linear regression was used to determine the association between the rs7512462 T risk allele and FEV1pp treatment difference. The robust linear regression was implemented in the R statistical package (http://CRAN.R-project.org) using the rlm library. All analyses of treatment response were adjusted for baseline FEV1pp measurement.

Two-sided p-values are provided in all cases, although the hypothesis of interest is that the T risk allele of rs7512462 is associated with worse response to treatment (i.e. single direction of interest).

A predictive model was developed to predict response to treatment with Ivacaftor based on FEV1pp baseline and rs7512462, using the discovery sample. A responder was defined as one who will see an improvement of 10 percentage points in FEV1 (FEV1pp difference>10). The predictive model was applied to the replication sample and computed the ROC and AUC along with a bootstrap confidence interval for the AUC to determine the generalizability of the model to an independent sample.

Results

SLC26A9 rs7512462 T allele is associated with reduced improvement in FEV1pp from Ivacaftor.

CF individuals with a G551D mutation display variable response to treatment with Ivacaftor in both the initial study of 11 individuals from Toronto enrolled in the Toronto open-label Ivacaftor study, and in 11 individuals in a replication sample. The variability in response is quite pronounced with observed treatment differences from baseline ranging from −6.25 to 28 FEV1 percentage points. The genotype distribution in the discovery and replication set were the same with T risk allele frequency of 0.68.

Figure 2:
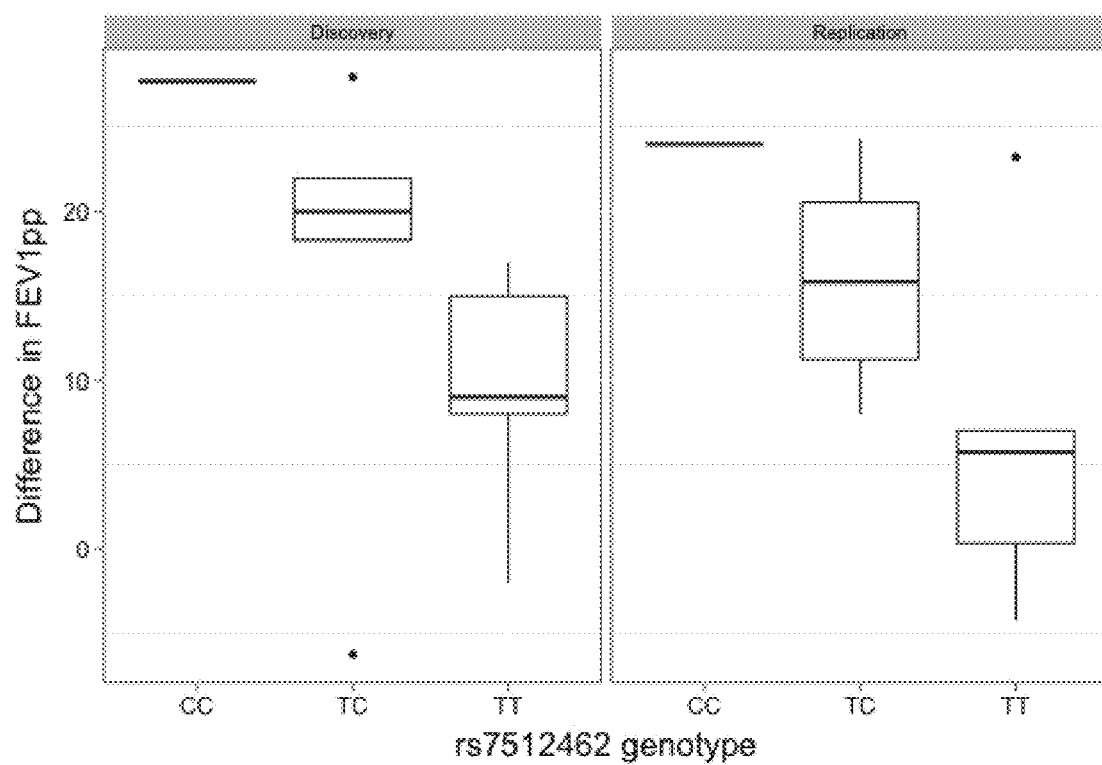
FIG. 2 depicts boxplots of FEV1pp treatment difference, wherein the left panel corresponds to the discovery set, and right panel corresponds to the replication phase.

FIG. 2 displays boxplots showing the distribution of treatment difference by rs7512462 genotype for discovery (FIG. 2, left panel) and replication (FIG. 2, right panel) sets. The difference is computed as average FEV1pp at follow-up measures minus baseline, and presented as a function of SLC26A9 rs7512462 genotype.

Although almost all individuals on Ivacaftor see an improvement in their FEV1pp from baseline, in the discovery sample each rs7512462 T allele is associated with an improvement that is 8.96 (se=3.52) percentage points lower for the genotype with one less C allele (two-sided p=0.037 after adjustment for baseline FEV1pp). The replication sample displays the same relationship, with each rs7512462 T allele associated with an improvement that is 9.91 (se=2.36) percentage points lower (two-sided p=0.004 after adjustment for baseline FEV1pp).

To develop a model that can predict whether a CF individual with a G551D or other gating mutation will respond to treatment with Ivacaftor with an FEV1pp difference of >10 percentage points, the discovery sample was used to fit a model with baseline FEV1pp and rs7512462 genotype. The coefficient estimates from that model were then used to predict whether the individuals in the replication sample would show improvement of greater than 10 percentage points. The model estimated from the discovery set computed an individual's predicted treatment response, $\hat{y}_i$, as:

$$\hat{y}_i = 29.4647 - 0.0151 \times FEV1pp(\text{baseline})_i - 8.8015 \times (\text{\# of rs7512462 risk allele})_i \quad \text{(Equation 1)}$$

Figure 3:
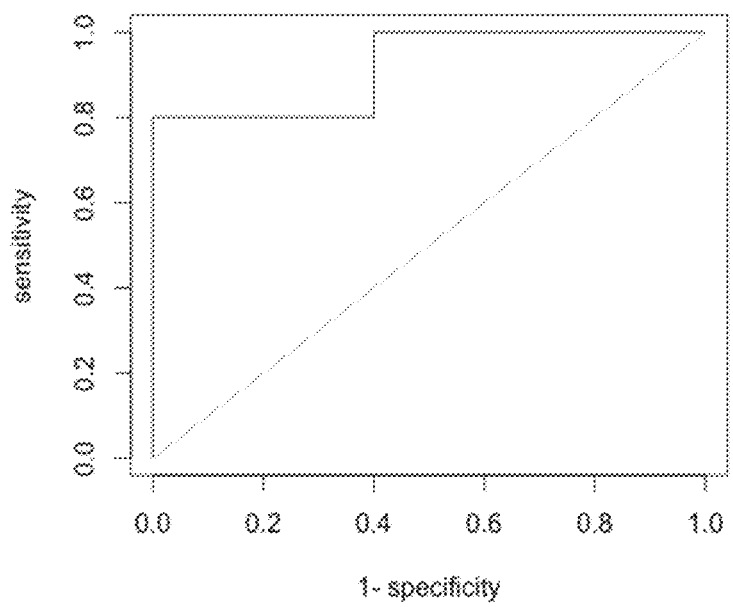
FIG. 3 depicts the Receiver Operating Characteristic Curve (ROC) for the response to treatment predictive model (Equation 1), applied to the independent replication data set.

FIG. 3 depicts the Receiver Operating Characteristic Curve (ROC) for the response to treatment predictive model (Equation 1), applied to the independent replication data set. The ROC suggests the model is highly predictive with AUC=0.92; the bootstrap 95% confidence interval ranged from 0.71 to 1, with a median AUC of 0.96.

Example 3

Other SNPs Associated with and Reduced Improvement from Ivacaftor in CF Patients with G551D Mutation Methods The association between FEV1pp difference and the SNP rs2282430 was assessed. Association of FEV1pp with the SNP rs2869027 was also assessed, the latter being a SNP in high LD with rs2282430, but having a higher allele frequency (i.e. it is potentially more informative). The same methodology as in Example 2 was employed.

rs2869027 and rs7512462 are uncorrelated and reside in different haplotype blocks. Rs2869027 and rs2282430 have D'=1, however the allele frequency of rs2282430 is less than 10%. Therefore, the association analysis was concentrated on rs2869027. This analysis was restricted to 13 CF patient samples in which both variants were genotyped.

Results

From the multivariate regression model for treatment response shown in Table 1 it is apparent that both rs7512462 and rs2869027 are both significantly associated (p=0.01 and 0.01, respectively).

TABLE 1

|  | Estimate | Std. Err | t value | p |
|---|---|---|---|---|
| (Intercept) | 30.14832066 | 7.97827673 | 3.7788011 | 0.004357043 |
| Baseline | −0.007261875 | 0.09003303 | −0.0806579 | 0.937479155 |
| rs7512462 | −8.077912133 | 2.5200578 | −3.2054472 | 0.01073705 |
| rs2869027 | −5.957153705 | 1.97056992 | −3.0230613 | 0.014407688 |

The same significant result holds for Saknorm, with p=0.03 and 0.02, respectively, as shown in Table 2.

TABLE 2

|  | Estimate | Std. Err | t value | p |
|---|---|---|---|---|
| (Intercept) | 1.2031542 | 0.201013 | 5.985454 | 9.40E−08 |
| rs7512462 | −0.3000064 | 0.1362947 | −2.20116 | 3.12E−02 |
| rs2869027 | −0.3512679 | 0.1444454 | −2.431838 | 1.77E−02 |

Defining a new covariate that represents a score of the number of risk alleles across the two SNPs, which can range from 0 to 4, it was observed that each additional risk allele across either SNP is a significant predictor of lung disease or treatment response (p=0.001 and p=0.0005, respectively). These findings suggest that independent variants that affect net SLC26A9 activity contribute to response to treatment, and to CF lung disease.

Example 4

Expression Studies

Expression profiles of SLC26A9 and CFTR in human tissues is consistent with the modification of disease severity in the CF lung. Both genes are expressed in CF-affected tissues including lung based on electrophysiological studies and on current comprehensive RNA expression databases (such as GTEX; www.gtexportal.org).

Example 5

CFTR-Mediated Current in Phe508del CF-Monolayers with VX-809 Treatment is Dependent on SLC26A9 rs7512462 Genotype Methods The primary human bronchial epithelial cells were obtained from 11 CF lung explants homozygous for the Phe508del CFTR mutation. SLC26A9 rs7512462 genotypes included n=3 with CC, n=5 with CT and n=3 with TT. Cell monolayers were mounted in a circulating Ussing chamber (Physiological Instruments Inc), maintained at 37° C. and continuously perfused with buffer at pH7.4 (with 126 mM NaCl, 24 mM NaHCO$_3$, 2.13 mM K2HPO4, 0.38 mM KH2PO4, 1 mM MgSO4, 1 mM CaCl2, 10 mM glucose) with symmetrical chloride concentrations in apical and basolateral chambers, and constant gassing with 5% CO2 and 95% 02. Transepithelial voltage was recorded and resistance was measured, following brief 1 µA current pulses every 30 seconds to obtain calculated equivalent short-circuit currents (Ieq). CFTR function was assessed following inhibition of the epithelial Na+ channel with amiloride (100 µM, Spectrum Chemical Mfg Corp) as forskolin (10 µM, Sigma Alrich)-activated currents (Δleq-forskolin; µA/cm2) in monolayers treated with lumacaftor (VX-809; 3 µM) or with DMSO (vehicle), for 48 h.

Results

Given that CF lung disease severity was influenced by SLC26A9 genotype in individuals where mutant CFTR (G551D) is known to successfully traffic to the apical surface, where effects were enhanced upon potentiation, we asked whether SLC26A9 would also influence responses to CFTR-directed therapies aimed at improved folding and trafficking of mutant CFTR to the apical surface of epithelial cells.

Primary human bronchial epithelial monolayers of 11 individuals with CF, homozygous for Phe508del, were assessed in an Ussing chamber following 24 hours exposure to vehicle alone (control) or the corrector drug, VX-809.

Figure 4:
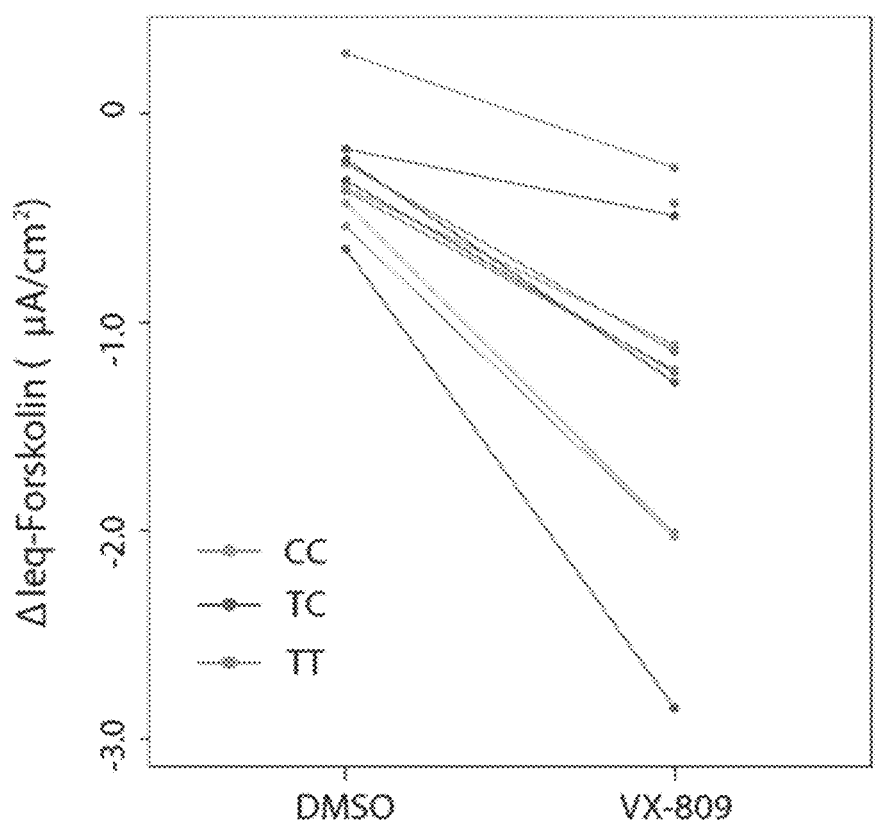
FIG. 4 depicts individual trajectories of Aleq-forskolin measures with vehicle followed by VX-809 treatments coded by rs7512462 genotype.

FIG. 4 depicts individual trajectories of Δleq-forskolin measures with vehicle followed by VX-809 treatments, coded by rs7512462 genotype (one sample treated with VX-809 had a missing baseline measurement). Forskolin-stimulated currents mediated by CFTR (measured as change in current after application of forskolin, Δleq-forskolin) were increased following treatment with corrector VX-809 (FIG. 4, more negative values correspond to more CFTR activity).

Figure 5:
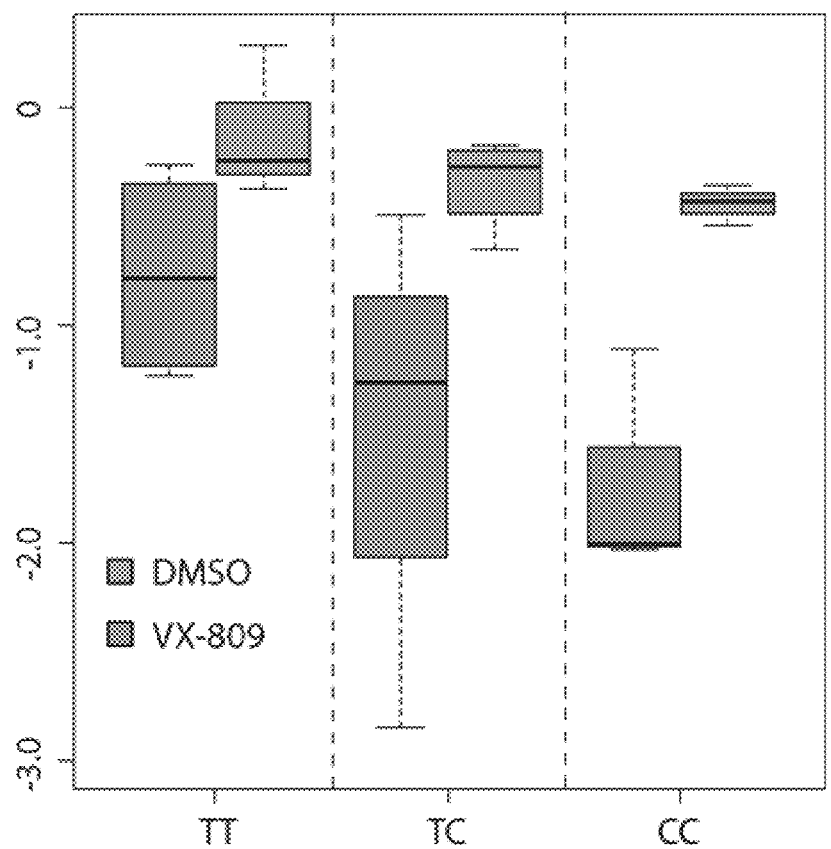
FIG. 5 depicts boxplots of the Aleq-forskolin with VX-809 treatment (lower left bars in each column) and DMSO vehicle measurements (upper right bars in each column) stratified by rs7512462 genotype.

FIG. 5 depicts boxplots of the Δleq-forskolin with VX-809 treatment. Differences in residual CFTR-mediated current across the rs7512462 genotypes in the cultures without drug treatment (DMSO, n=10) did not reach statistical significance (p=0.09, −0.17 µA/cm2 Δleq-forskolin per C protective allele, FIG. 5, upper right bars in each column). However, CFTR-medicated currents generated with corrector VX-809 treatment (n=11, FIG. 4), indicated that each additional C allele of rs7512462 was associated with improved function (p=0.02, −0.49 µA/cm2 Δleq-forskolin per C protective allele, FIG. 5, lower right bars in each column). Taken together with the G551D findings above, the rs7512462-SLC26A9 allele effect upon treatment with corrector drug would be consistent with modification of surface-localized Phe508del CFTR.

Example 6

Discussion

Treatment of CF, using CFTR-directed therapeutics or gene therapy, has great potential to treat all individuals with CF-causing CFTR mutations. The potential for these therapies is evidenced by the improved outcomes in individuals with at least one G551D allele on Ivacaftor, or those homozygous for Phe508del on Lumacaftor-Ivacaftor combination therapy. However, why different individuals with a G551D allele or other gating mutation (or Phe508del homozygotes on combination therapy) can differ so dramatically in their response to treatment has not been well understood.

Only a small proportion of individuals with gating mutations, such as G551D, have been included in studies of modifier genes to date, the proportion being reflective of the distribution of CFTR genotypes associated with severe pancreatic disease in the North American and European CF populations.

Here an explanation for that variability in treatment response is provided. Despite previous observations to the contrary indicating that there is no association between SLC26A9 and CF lung disease (Corvol et al 2015; Wright et al 2011; Li et al 2014), it is surprisingly shown herein that SLC26A9 is indeed a modifier of CF lung disease. It is shown that:

1) SLC26A9 rs7512462 or rs2869027 are a modifiers of CF lung disease in individuals with at least one G551D allele or other gating mutation (i.e. the SLC26A9-lung function relationship is dependent on CFTR genotype)

2) In individuals with a G551D allele or another gating mutation, response to treatment with Ivacaftor differs depending on SLC26A9 rs7512462 or rs2869027 genotype 3) SNPs in the 3' UTR also contribute to treatment response and do so independently of rs7512462.

Using the resources of the Canadian CF Gene Modifier study, it is unexpectedly shown that the chloride channel SLC26A9 is a modifier of lung function in 56 individuals with CFTR gating mutations (p=0.05), mutations that result in CFTR protein at the cell surface, but not in individuals who are homozygous for the most common CFTR mutation Phe508del, which results in little to no CFTR protein at the cell surface. For carriers of gating mutations, it is shown that SLC26A9 is a significant predictor of response to treatment with Ivacaftor, where each additional T risk allele at rs7512462 is associated with an FEV1pp treatment response that is 8.96 (p=0.037, n=11) and 9.91 (p=0.004, n=11) percentage points lower in the discovery and replication samples, respectively.

rs7512462 is an intronic SNP in SLC26A9 that has been previously shown to account for almost 12% of the variability in a biomarker of exocrine pancreatic disease at birth (Miller et al 2015), and this same SNP has been shown to contribute to CF intestinal obstruction due to meconium ileus in genome-wide studies (Sun et al 2012). However, despite this and its established expression in human lung epithelia, SLC26A9 has shown no evidence of association with CF lung disease to date.

SLC26A9, among other functions, is a Cl/HCO$_3$ channel that physically interacts with CFTR (Chang et al 2009) in lung cells (Bertrand et al 2009). Studies in CFTR-deficient mice have shown that increased SLC26A9 activity can alleviate CF-associated morbidities in the gut (Liu et al 2015), while increased SLC26A9 activity in asthmatic mice prevented airway mucus plugging and variants in the 3' UTR have been shown to associate with asthma (Anagnostoulou et al 2012). Our results are particularly surprising given that SLC26A9 has not been detected as a modifier gene of CF lung disease in genome-wide association studies (Wright et al 2011; Corvol et al 2015) or in candidate gene studies (Li et al 2014). The conclusion drawn here is that one needs CFTR at the cell surface for SLC26A9 to have its modifying effect, and this only occurs in a minority of severe CFTR mutations, such as G551D. Evidence of association between lung disease and SLC26A9 in G551D mutation carriers but not in individuals homozygous for Phe508del provides support for this explanation.

Given that mice deficient in both the SLC26A9 and CFTR counterparts (homologues) exhibit more severe disease (i.e., the effect is at least partially cumulative), and given that the same T allele of rs7512462 has been previously associated with more severe GI disease, another conclusion that can be drawn is that risk alleles identified herein (i.e., the T allele of rs7512462 and the C allele of rs2869027) are markers of decreased SLC26A9 expression and activity relative to their counterpart protective alleles.

Since SLC26A9 interacts with CFTR at the cell surface increases in CFTR (e.g. via Ivacaftor) and/or SLC26A9 (e.g. marked by the rs7512462 C allele or the rs2869027 G allele) would provide more opportunity for SLC26A9 to have greater modifying effect, as evidenced in FIGS. 1 and 3. This finding is independent of which therapeutic increases CFTR, suggesting that SLC26A9 will be a modifier of treatment response for any therapy that increases CFTR protein that resides at or is directed to the cell surface (such as for Lumacaftor or Ivacaftor-Lumacaftor combination therapy that has shown efficacy in Phe508del homozygotes (Wainwright et al 2015). Accordingly, the findings presented herein can be generalized to any CFTR-directed therapeutic agent and any CF genotype (other than those in which there would be no possibility of restoring protein function). Likewise, the finding should be relevant to e.g. therapeutics based on gene therapy efforts to increase or restore CFTR.

With regard to Example 5, although rs7512462 does not show association with lung function in CF populations homozygous for Phe508del, it does appear to influence forskolin-stimulated CFTR currents in primary cell monolayers from CF patients upon treatment with a recently developed drug to restore Phe508del CFTR maturation and cell surface delivery.

That the SLC26A9 benefit is realized when CFTR is present at the apical membrane is insightful with regard to how modification may be occurring. In the airways, the presence of CFTR at the membrane appears necessary, possibly to enable interaction with SLC26A9 that is then further accommodated when CFTR is functioning. These notions are consistent with the rationale of ivacaftor treatment for G551D (wherein this potentiator drug is used to obviate the gating limitation imposed by the missense change), and with earlier studies showing that SLC26A9 can enhance CFTR channel function (Bertrand et al. 2009; Avella et al., 2011; Ousingsawat et al. 2011). Further, CF individuals with the homozygous Phe508del genotype would not show benefit in lung function from their respective SLC26A9 genotype (as we observed), without facilitation of mutant protein delivery and restoration of some CFTR function as should occur with the introduction of corrector drugs such as VX-809. Together these findings predict that SLC26A9 may influence airway outcomes in any therapeutic situation with increased apical-surface localized CFTR protein and therefore would be generalizable to pharmacological, gene therapy-driven or other efforts to increase or restore working CFTR.

In summary, these new findings indicate that SLC26A9 is a modifier of CF lung disease when there is CFTR at the cell surface (e.g. in the case of a gating mutation), and that SLC26A9 is also a modifier of treatment response for any CFTR-directed therapy or therapeutic that increases CFTR or CFTR activity at the cell surface.

The ability to predict whether an individual will respond better or worse to treatment with CFTR-directed therapies allows for personalized approaches to therapy, assists in clinical trial design, and provides for more informed cost-benefit analyses of CFTR-directed therapeutics, which can be costly. Knowledge that SLC26A9 is a modifier of treatment response suggests SLC26A9 is an alternative or complimentary therapeutic target, particularly for patients with CFTR mutations that maintain some residual protein at the cell surface, or where mis-trafficked CFTR can be coaxed to the epithelial cell surface.

Knowing a CF patient's modifier gene status at SLC26A9 can assist clinicians to make decisions about prescribing costly CFTR-directed therapeutics, and can direct personalized approaches to therapy that may require additional/alternative therapies in risk allele carriers who would be predicted to respond poorly to treatment. Knowledge that rs7512462 (and/or together with variants in the 3' UTR including rs2869027) is a marker for treatment response can lead to improved drug efficacy and can provide insight to direct and optimize drug treatment; for example, those homozygous for the SLC26A9 risk allele may benefit from greater drug dosage, or more frequent administration. Knowledge of rs7512462 or rs2869027 genotype also imparts important information for individuals designing clinical trials for future CF therapeutics and for more informed cost-benefit analyses for payers of costly CFTR-directed therapeutics.

The findings presented herein are extremely consistent across samples as evidenced by the AUC of the predictive model in the external validation/replication sample. These results provide evidence that SLC26A9 will be an important modifier of CFTR-directed therapies.

The clinical utility of genetic markers has been questioned. Here, examples of markers are provided that can further personalize therapeutic approaches to CF and improve outcomes, potentially, for all CF patients.

In view of the forgoing, SLC26A9 is itself a novel therapeutic target. As a therapeutic target it could complement future gene therapies or CFTR directed approaches; or be a therapeutic target in its own right for less severe CFTR mutations or other mutations with CFTR protein already at the epithelial cell surface.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

[1] Ramsey B W, Davies J, McElvaney N G, Tullis E, Bell S C, Dřevinek P, Griese M, McKone E F, Wainwright C E, Konstan M W, Moss R, Ratjen F, Sermet-Gaudelus I, Rowe S M, Dong Q, Rodriguez S, Yen K, Ordoñez C, Elborn J S; VX08-770-102 Study Group. A CFTR potentiator in patients with cystic fibrosis and the G551D mutation. N Engl J Med. 2011 Nov. 3; 365(18):1663-72. doi: 10.1056/NEJMoa1105185.

[2] Wainwright C E, Elborn J S, Ramsey B W, Marigowda G, Huang X, Cipolli M, Colombo C, Davies J C, De Boeck K, Flume P A, Konstan M W, McColley S A, McCoy K, McKone E F, Munck A, Ratjen F, Rowe S M, Waltz D, Boyle M P; TRAFFIC and TRANSPORT Study Groups. Lumacaftor-Ivacaftor in Patients with Cystic Fibrosis Homozygous for Phe508del CFTR N Engl J Med. 2015 May 17. [Epub ahead of print]

[3] Wright, F, Strug, L J, Doshi, V, Commander, C, Blackman, S, Sun, L, Berthiaume, Y, Cutler, D, Li, W, Collaco, M, Corey, M, Dorfman, R, Goddard, K, Green, D, Kent, J, Lange, E, Lee, S, Cojocaru, A, Luo, J, Mayhew, G, Naughton, K, Pace, R, Pare, P, Rommens, J, Sandford, A, Stonebraker, J, Sun, W, Taylor, C, Vanscoy, L, Zou, F, Blangero, J, Zielenski, J, O'Neal, W, Drumm, M, Durie, P, Knowles, M R. and Cutting, G. Genome-wide association and linkage identify modifier loci of lung disease severity in cystic fibrosis at 11p13 and 20q13.2. Nature Genetics. 43: 539-546. 2011.

[4] Sun, L, Rommens, J M, Corvol, H, Li, W, Li, X, Chiang, T, Lin, F, Dorfman, R, Busson, P, Parekh, R, Zelenika, D, Blackman, S, Corey, M, Doshi, V, Henderson, L, Naughton, K, O'Neal, W K, Pace, R G, Stonebraker, J R, Wood, S D, Wright, F A, Zielenski, J, Clement, A, Drumm, M L, Boelle, P Y, Cutting, G R, Knowles, M R, Durie, P R, Strug, L J. Multiple apical plasma membrane constituents are associated with Meconium Ileus in Cystic Fibrosis. Nature Genetics. 44: 562-9. 2012.

[5] Blackman, S M, Commander, C W, Watson, C, Arcara, K, Strug, L J, Stonebraker, J R, Wright, F A, Rommens, J M, Sun, L, Pace, R G, Norris, S A, Durie, P R, Drumm, M L, Knowles, M R, Cutting, G R. Genetic modifiers of cystic fibrosis-related diabetes. Diabetes 62: 3627-35. 2013.

[6] Li, W, Soave, D, Miller, M R, Keenan, K, Lin, F, Gong, J, Chiang, T, Stephenson, A, Durie, P, Rommens, J, Sun, L, Strug, L J. Unraveling the Complex Genetic Model for Cystic Fibrosis: Pleiotropic Effects of Gene Modifiers on Early C F-Related Morbidities. Human Genetics. 133: 151-61. 2014.

[7] Soave D, Miller M, Keenan K, Li W, Gong J, Ip W, Accurso F, Sun L, Rommens J, Sontag M, Durie P, Strug L J. Prenatal exocrine pancreatic disease causes cystic fibrosis-related diabetes: A mendelian randomization study. Diabetes, 63(6): 2114-9. 2014.

[8] Miller, M R, Soave, D, Li, W, Gong, J, Pace, R G, Boelle, P Y, Cutting, G R, Drumm, M L, Knowles, M R, Sun, L, Rommens, J M, Accurso, F, Durie, P R, Corvol, H, Levy, H, Sontag, M K, Strug, L J. Variants in Solute Carrier SLC26A9 Modify Prenatal Exocrine Pancreatic Damage in Cystic Fibrosis. Journal of Pediatrics. PMID: 25771386. 2015.

[9] Soave, D, Corvol, H, Panjwani, N, Gong, J, Li, W, Boelle, P Y, Durie, P, Paterson, A D, Rommens, J M, Strug, L J*, Sun, L.* A joint location-scale test improves power to detect associated SNPs, gene-sets and pathways. The American Journal of Human Genetics. Accepted for Publication.

[11] Bertrand C A, Zhang R, Pilewski J M, Frizzell R A. SLC26A9 is a constitutively active, CFTR-regulated anion conductance in human bronchial epithelia. J Gen Physiol. 133:421-38. 2009.

[12] Bobadilla J L, Macek M, Fine J P, Farrell P M. Cystic Fibrosis: A worldwide analysis of CFTR mutations—Correlation with incidence data and application to screening. Human Mutations. 19:575-606. 2002.

[13] Bompadre S G, Sihma Y, Li M, Hwang T C. G551D and G1349D, Two CF-associated mutations in the signature sequences of CFTR, Exhibit Distinct Getting Defects. J Gen Physiol 2007 129:285-298.).

[14] Mall M A, Galietta L V J. Targeting ion channels in cystic fibrosis. J Cystic Fibrosis (2015): in press.

[15] PCT Publication WO2003/074664A2.

[16] Corvol, Blackman et al Genome-wide association meta-analysis identifies five modifier loci of lung disease severity in cystic fibrosis. Nature Communications. Accepted for publication

[17] Alton E W F W et al Repeated nebulisation of non-viral CFTR gene therapy in patients with cystic fibrosis: a randomised, double-blind, placebo-controlled, phase 2b trial. The Lancet ePub online Jul. 3, 2015.

[18] Taylor C et a. A novel lung disease phenotype adjusted for mortality attrition for cystic fibrosis genetic modifier studies. Pediatric Pulmonol 2011 46(9): 857-69.

[19] Dorfman et al Modulatory effect of the SLC9A3 gene on susceptibility to infections and pulmonary function in children with cystic fibrosis. Pediatric Pulonol 2011 46: 385-92.

[20] Kulich et al Disease-specific reference equations for lung function in patients with cystic fibrosis. Am J Respir Crit Care Med 2005 172(7), 885-891.

[21] Chang et al Slc26a9 is inhibited by the R-region of the cystic fibrosis transmembrane conductance regulator via the STAS domain. J Biol Chem. 2009 Oct. 9; 284(41): 28306-18.

[22] Liu et al Loss of SLC26A9 Anion Transporter Alters Intestinal Electrolyte and HCO3(−) Transport and Reduces Survival in CFTR-deficient Mice. Pflugers Arch. 2015 June; 467(6):1261-75.

[23] Anagnostooulou et al SLC26A9-mediated Chloride Secretion Prevents Mucus Obstruction in Airway Inflammation. J Clin Invest. 2012 Oct. 1; 122(10): 3629-3634.

[24] Avella, M., Loriol, C., Boulukos, K., Borgese, F. and Ehrenfeld, J. (2011) SLC26A9 stimulates CFTR expression and function in human bronchial cell lines. *J. Cell Physiol.*, 226, 212-223.

[25] Ousingsawat, J., Schreiber, R. and Kunzelmann, K. (2011) Differential Contribution of SLC26A9 to Cl− conductance in polarized and non-polarized epithelial cells. *Cell Physiol. Biochem.*, 227, 2323-2329.

All references cited herein are incorporated by reference in their entireties for all purposes as if explicitly set forth herein.

The invention claimed is:

1. A method of treating cystic fibrosis (CF) lung disease in a CF patient with a CFTR-directed therapy, the method comprising steps of:
   determining that said CF patient has a genotype CC or TC in single nucleotide polymorphism (SNP) rs7512462; and
   administering said CFTR-directed therapy to said CF patient,
   wherein the CFTR-direct therapy comprises Ivacaftor, Lumacaftor, Ataluren, or any combination thereof.

2. The method of claim 1, wherein said step of determining comprises determining that said CF patient has the genotype CC in the SNP rs7512462.

3. The method of claim 1, wherein the CF patient comprises at least one CFTR mutation resulting in residual CFTR protein at the cell surface.

4. The method of claim 3, wherein the at least one CFTR mutation comprises a CFTR gating mutation.

5. The method of claim 4, wherein the CFTR gating mutation is G551D.

6. The method of claim 1, wherein the CF patient comprises a Phe508del mutation in CFTR.

7. The method of claim 1, wherein the CFTR-directed therapy comprises the Ivacaftor.

8. The method of claim 1, wherein the CFTR-directed therapy comprises the Lumacaftor.

9. The method of claim 1, wherein the CFTR-directed therapy comprises a combination of Ivacaftor and Lumacaftor.

10. The method of claim 1, wherein the CFTR-directed therapy comprises the Ataluren.

* * * * *